United States Patent [19]

Lin et al.

[11] Patent Number: 5,428,442
[45] Date of Patent: Jun. 27, 1995

[54] INSPECTION SYSTEM WITH IN-LENS, OFF-AXIS ILLUMINATOR

[75] Inventors: Lawrence H. Lin, Alamo; Victor A. Scheff, Alameda, both of Calif.

[73] Assignee: Optical Specialties, Inc., Fremont, Calif.

[21] Appl. No.: 130,281

[22] Filed: Sep. 30, 1993

[51] Int. Cl.[6] .......................................... G02B 27/42
[52] U.S. Cl. .................................................. 356/237
[58] Field of Search ............................... 356/237, 376

[56] References Cited

U.S. PATENT DOCUMENTS

| Re. 33,956 | 6/1992 | Lin et al. | 250/550 |
|---|---|---|---|
| 4,197,011 | 4/1980 | Hudson | 356/354 |
| 4,636,069 | 1/1987 | Balasubramanian | 356/376 |
| 4,806,774 | 2/1989 | Lin et al. | 356/237 |
| 4,895,446 | 1/1990 | Maldari et al. | 356/337 |
| 4,900,940 | 2/1990 | Nakamura | 356/376 |
| 5,177,559 | 1/1993 | Batchelder et al. | 356/237 |
| 5,264,912 | 11/1993 | Vaught et al. | 356/237 |

OTHER PUBLICATIONS

Watkins, L. S., "Inspection of Integrated Circuit Photomasks with Intensity Spatial Filters," Proceedings of the IEEE, vol. 57, No. 9, pp. 1634–1639, Sep. 1969.

Primary Examiner—Richard A. Rosenberger
Attorney, Agent, or Firm—Stoel Rives Boley Jones & Grey

[57] ABSTRACT

An inspection system (2) employs a beam of monochromatic light (12) that travels through a Fourier transform lens (16) before striking a specimen wafer (4) at an angle ($\Theta$) with respect to the normal (26) of the specimen wafer (4) to produce diffracted light (28b) and 28c) that has a broad spatial frequency spectrum which can be selectively filtered to produce a dark field image pattern of the various sized defects in an inspection area (22) of the wafer. The nearly collimated beam of monochromatic light strikes the wafer at an angle ($\Theta$) with respect to the normal of the wafer of between zero degrees and a predetermined maximum angle. For the inspection system disclosed, the predetermined maximum angle is the angle formed when the beam of monochromatic light is as far away from the optic axis as possible yet still within the numerical aperture of the Fourier transform lens (16). Moreover, if a specific range of defect sizes is anticipated, the system can be optimized by setting the angle ($\Theta$) at which the collimated beam of monochromatic light strikes the wafer to the angle ($\Theta$) which allows the system to collect those spatial frequencies which are best representative of the anticipated range of defects sizes.

21 Claims, 5 Drawing Sheets

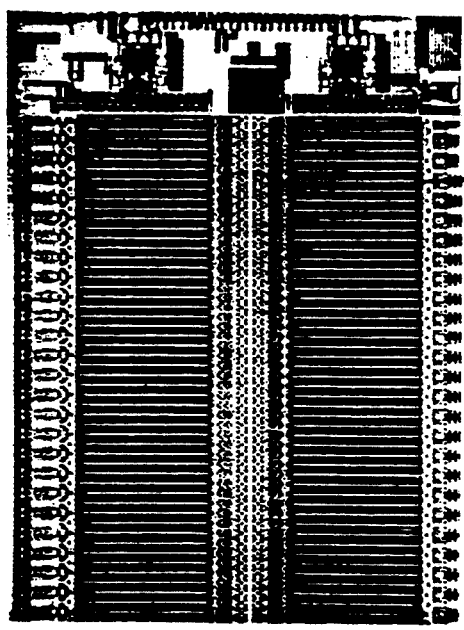
FIG. 2A
FIG. 2B
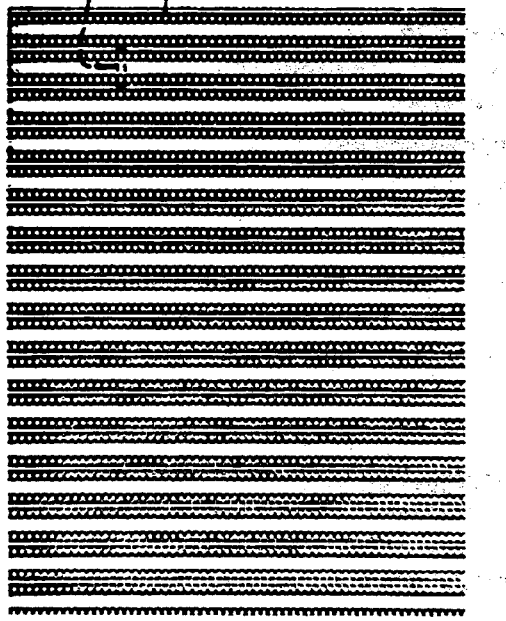
FIG. 2C
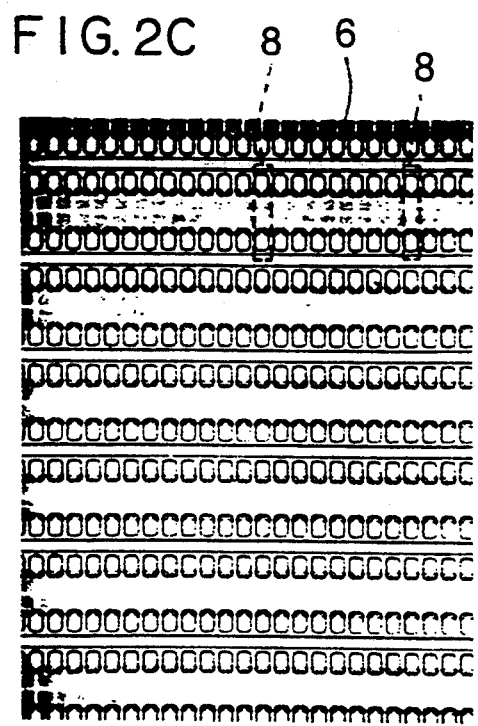

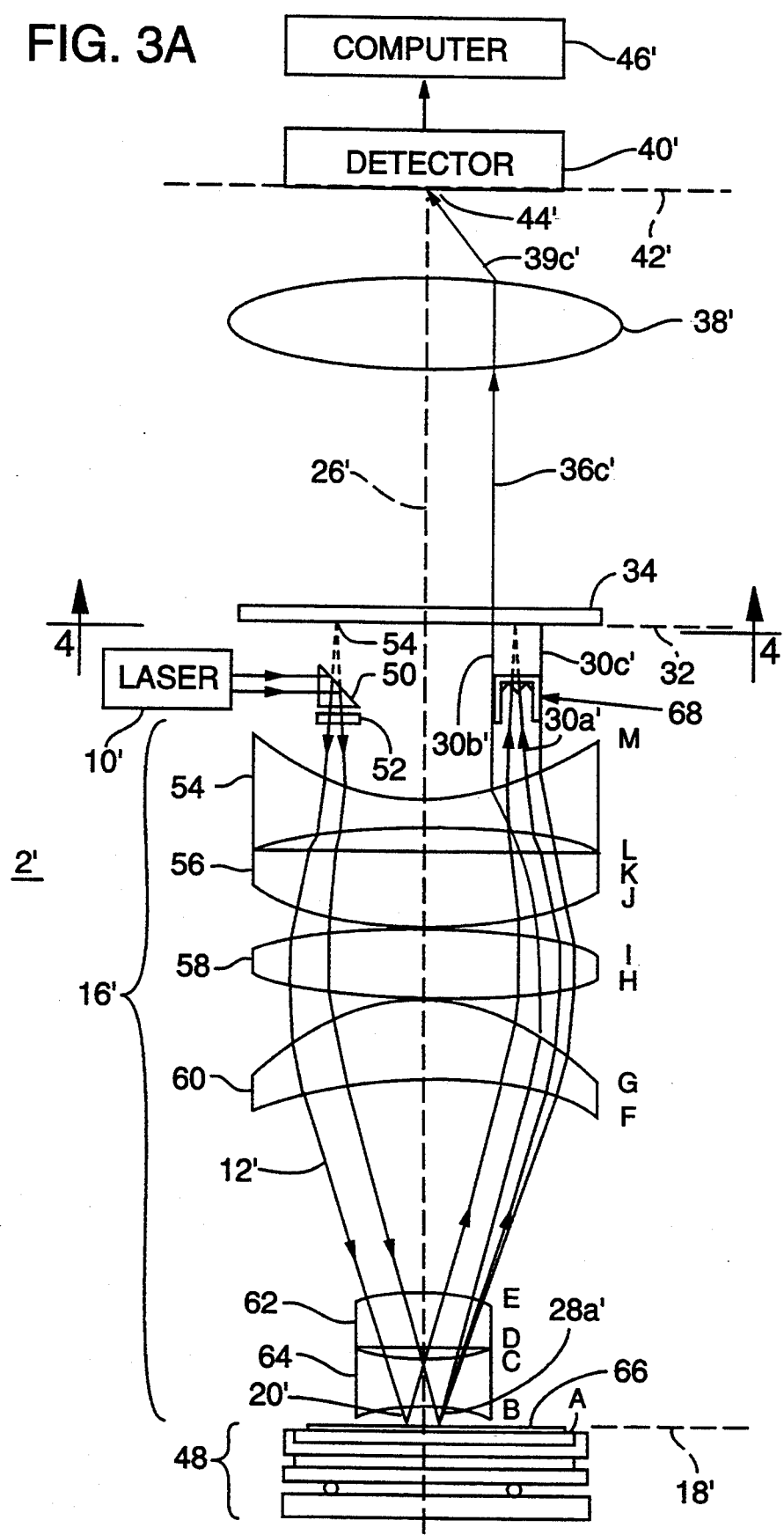

INSPECTION SYSTEM WITH IN-LENS, OFF-AXIS ILLUMINATOR

TECHNICAL FIELD

The present invention relates to an apparatus and a method for locating defects in items having regular patterns and, in particular, to an inspection system with an in-lens, off-axis illuminator which may be used to inspect surfaces having fine repetitive patterns thereon.

BACKGROUND OF THE INVENTION

The detection of defects on patterned wafers is a critical problem in the semiconductor industry. Defects in one or more of the photolithographic patterns can produce nonfunctioning or substandard devices. It is important to identify the type and characteristics of any defects in the integrated circuits at various processing stages so that the cause of the defects can be corrected before it adversely affects the yield.

In the prior art, there are many ways to locate defects on the surface of a semiconductor wafer. One typical defect location method is image analysis of dark field images. There are presently several different methods of illuminating the surface of the wafer so that defects can be found. Generally, these illumination methods fall into one of two classes: the in-lens, on-axis illumination technique and the off-lens, off-axis illumination technique.

The terms "in-lens" and "off-lens" refer to whether an incident beam of light produced by an inspection system travels through or does not travel through, respectively, an inspection (e.g., Fourier transform) lens before striking the surface of a semiconductor wafer. Similarly, the terms "on-axis" and "off-axis" refer to whether an illumination beam, a Fourier transform lens, and the semiconductor wafer under inspection are all positioned or are not positioned, respectively, along an axis.

One such prior art reference is U.S. Pat. No. Re. 33,956 entitled INSPECTION SYSTEM FOR ARRAY OF MICROCIRCUITS DIES HAVING REDUNDANT CIRCUIT PATTERNS, which is hereby incorporated by reference for its teachings in optics and the inspection of semiconductor wafers, describes an in-lens, on-axis illumination technique. This system uses an illumination beam, a Fourier transform lens, an inverse Fourier transform lens, and a semiconductor wafer which are all positioned along an optic axis.

The system forms a dark field image of an area on the wafer at a distant image plane. In this system, spatial frequencies corresponding to the repetitive patterns are selectively attenuated in the dark field image by inserting a spatial filter at a Fourier transform plane between the two lenses. The resulting image accentuates irregularities on the surface of the integrated circuit, such as may result from defects in the pattern.

In this system, the illuminating beam illuminates the wafer through the Fourier transform lens. Thus, light scattered and reflected by the lens adds background noise to the image. The light scattering problem can be reduced by surface cleaning of the lens, coating of the lens, and proper selection of the lens materials. In addition, specular reflections from the Fourier transform lens also add background noise to the image. This background noise can be reduced significantly by using an anti-reflection coating on the lens and by using judiciously sized and placed stops along the optical axis. Nonetheless, background noise resulting from specular reflections will reach the detection device and does reduce the sensitivity of the detection system.

This system collects spatial frequencies of the defects in the wafer which are symmetrically disposed about an origin in the Fourier transform plane that includes two orthogonal axes and four separate quadrants. Because the defects in the wafer can usually be considered planer, the spatial frequency spectrum associated with these defects is symmetrical along both axes in the Fourier transform plane. Thus, this system collects symmetrical spatial frequency components which provide redundant defect information and limits the highest spatial frequency this system can collect. Accordingly, this inspection system may be less sensitive to some relatively small sized defects in the wafer which have relatively more high frequency components.

An example of an off-lens, off-axis illumination scheme is given in U.S. Pat. No. 5,177,559 entitled DARK FIELD IMAGING DEFECT INSPECTION SYSTEM FOR REPETITIVE PATTERN INTEGRATED CIRCUITS, which is hereby incorporated by reference for its teachings in optics and the inspection of semiconductor wafers.

This system forms a dark field image of an area on the wafer. In this system, a semiconductor wafer is illuminated with a light beam at a grazing angle of incidence of between 8 degrees and a predetermined maximum angle with respect to the wafer surface. Light scattered at angles within a given range about the normal to the wafer surface is collected by a lens system which spatially filters the collected light so as to attenuate spatial frequency components corresponding to repetitive patterns. The remaining light is focused and forms an image which accentuates irregularities on the surface of the wafer such as may result from defects in the pattern.

In this system, most of the reflected light reflects away from, rather than toward, the lens system. Only a very small percentage of the total reflected light scatters at angles normal to the wafer so that the lens system can collect this scattered light. Thus, to collect a sufficient amount of scattered light, the lens system is usually located very close to the surface of the wafer. Typically, in applications requiring detection of submicron defects, the space between the lens system and the wafer surface is such that introducing the illumination beam is difficult and limits the lens design forms available for the Fourier transform lens (e.g., lens size, numerical aperture, and working distance).

This system collects spatial frequencies of the defects which are in the higher range. The collected spatial frequencies in the higher range are collected from within one of the four quadrants within the Fourier transform plane; therefore, this inspection system fails to use the maximum collection capability of the lens system. It also means that this inspection system can be less sensitive to some relatively large sized defects that have relatively low frequency components.

SUMMARY OF THE INVENTION

With the foregoing in mind, it is the primary object of the present invention to provide a reliable inspection system which can determine the presence of a very broad range of different sized defects in the manufacture of microcircuits of the type that comprises a plurality of die circuits patterns located on a wafer.

Another object of this invention is to provide such a system that collects and processes a broad range of spatial frequency components from the low, the mid-level, and the relatively high spatial frequencies in the Fourier transform plane.

A further object of this invention is to provide such a system that collects all of the broad range of spatial frequency components substantially from only one of the four quadrants in the Fourier transform plane.

Still another object of the present invention to is provide an inspection system with an in-lens, off-axis illuminator which does not suffer from residual specular reflection.

The present invention relates to a method and system for use in the manufacture of microcircuits and is described herein only by way of example with reference to a real-time inspection system for detecting defects in surfaces of semiconductor wafers of the type that includes many redundant circuit patterns.

The preferred embodiment of the inspection system employs a beam of monochromatic light that travels through a Fourier transform lens before striking the specimen wafer at an angle with respect to the normal of the specimen wafer to produce diffracted light that contains a broad spatial frequency spectrum which can be selectively filtered to produce a dark field image pattern of the various sized defects in an inspection area of the wafer.

Specifically, a laser generates a beam of monochromatic light onto a reflector, such as a prism or mirror, which reflects the beam of monochromatic light onto a Fourier transform lens. The Fourier transform lens is located between the laser and the specimen wafer and provides a nearly collimated beam of monochromatic light to the inspection area on the specimen wafer which encompasses a plurality of die circuit patterns. The nearly collimated beam of monochromatic light strikes the specimen wafer at an angle with respect to the normal of the wafer of between zero degrees and a predetermined maximum angle. The Fourier transform lens captures any light diffracted from the inspection area at angles with respect to the normal of the specimen wafer of between zero degrees and the predetermined maximum and generates therefrom Fourier transformed light from the captured light. The predetermined maximum angle is generally given by the numerical aperture of the Fourier transform lens.

A spatial filter collects the Fourier transformed light and attenuates the spatial frequency components which conform to the spatial frequency components of an error-free reference pattern corresponding to the die circuit patterns. The spatial frequency components not blocked by the spatial filter ultimately strike the surface of a two-dimensional photodetector array which detects the presence of light corresponding to defects in only the inspection area.

The inspection of all possible defects; in the portions of the wafer surface having many redundant circuits patterns is accomplished by mounting the wafer onto a two-dimensional translation stage and moving the stage so that the inspection area defined by the beam of monochromatic light continuously scans across the wafer surface until the desired portions of the wafer surface have been illuminated. The use of time delay integration techniques permits continuous stage movement and inspection of the portions of the wafer surface having many redundant circuit patterns in a stripe-to-stripe serpentine scan fashion.

The inspection system can also be optimized to detect a specific defect type and size. By moving the angle with respect to the optic axis at which the collimated beam of monochromatic light strikes the wafer, the system will collect a different spatial frequency spectrum at each angle for which the collimated beam of light strikes the wafer surface. Subsequently, if a specific range of defect sizes is anticipated for a group of wafers to be inspected, the system can be optimized by setting the angle to the one which allows the system to collect those spatial frequencies which are best representative of the anticipated range of defects sizes.

BRIEF DESCRIPTION OF THE DRAWINGS

Additional objects and advantages of the present invention will be apparent from the following detailed description of preferred embodiments thereof, which proceeds with reference to the accompanying drawings, wherein:

FIGS. 2A–2C are photographs of a portion of an exemplary single die of the semiconductor wafer of FIG. 1B showing within such a die a highly redundant circuit pattern for connectively increasing magnifications;

FIG. 3A is a more detailed block diagram of the wafer inspection system which includes an embodiment of the invention;

DETAILED DESCRIPTION OF PREFERRED EMBODIMENTS

An inspection system according to the present invention employs a combination of dark field imaging, Fourier spatial filtering, and an in-lens, off-axis illuminator to detect a broad range of different sized pattern defects in items, such as semiconductor wafers, which exhibit fine-featured repetitive patterns. The principles of Fourier spatial filtering are described in a paper by L. S. Watkins entitled "Inspection of Integrated Circuit Photomasks with Intensity Spatial Filters" *Proceedings of the IEEE*, Vol. 57, No. 9, September 1969, which is hereby incorporated by reference.

While this system is described in the context of a semiconductor wafer inspection system, it is contemplated that it may be used for inspecting other items having repetitive patterns, such as charge-coupled device (CCD) panels, photolithographic masks used to manufacture semiconductor devices, or shadow masks for color cathode-ray tubes. Moreover, in FIGS. 1 and 3, the paths of the incident light and diffracted light are illustrated by ray tracing, wherein the traced rays are shown in solid lines. These lines represent the paths of incident or diffracted light but do not represent points on the object being imaged.

Figure 1A:
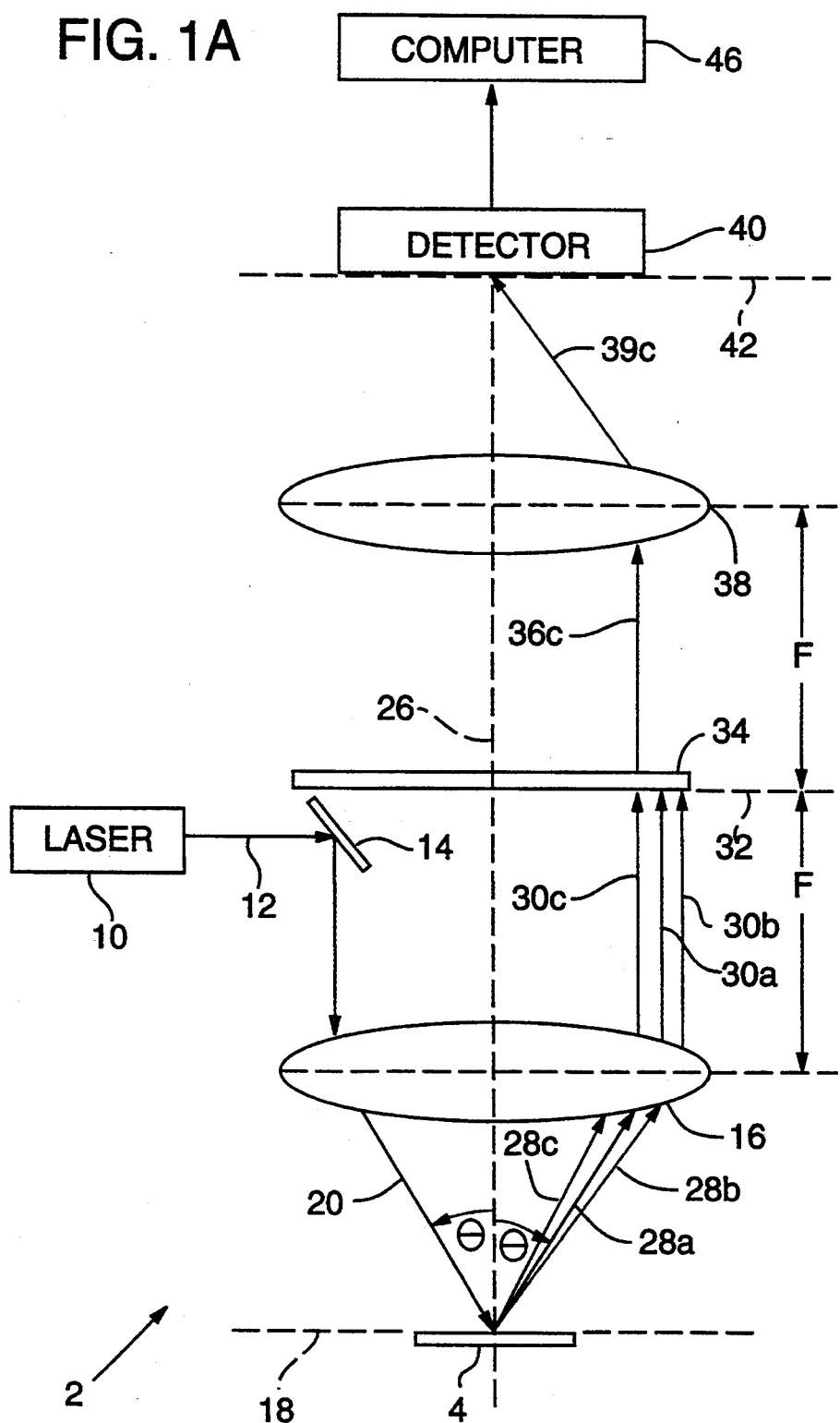
FIG. 1A is a block diagram of a wafer inspection system which includes an embodiment of the invention.
Figure 1B:
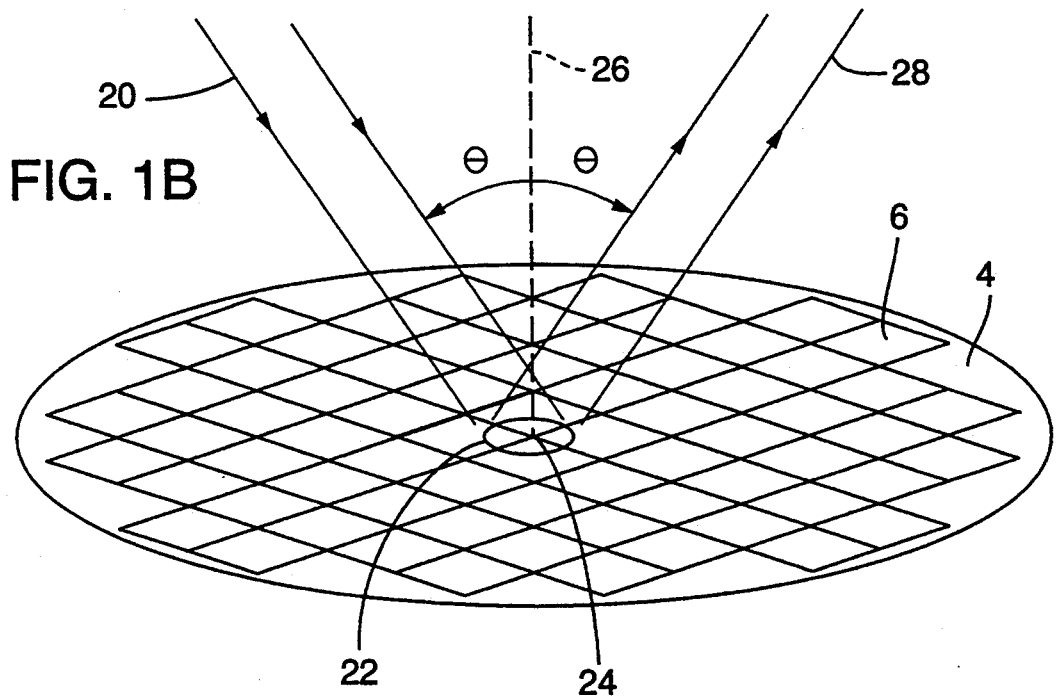
FIG. 1B is a perspective drawing which is useful to the manner in which the semiconductor wafer is illuminated by the inspection system shown in FIG. 1A.

FIG. 1A is a simplified schematic diagram of an embodiment of an inspection system 2 of the present invention that is designed to detect semiconductor wafer defects having a diameter of about 0.1 micron or larger in the presence of a periodic structure comprising many redundant circuit patterns. FIG. 1B is a diagram of a semiconductor wafer 4 of the type the inspection system 2 is designed to inspect. Semiconductor wafer 4 includes a regular array of normally identical dies 6 of which each has one or more redundant circuit patterns along each of the X-axis and the Y-axis. Each die 6 is typically of square shape with about a 1 centimeter side. FIGS. 2A-2C are photographs of an exemplary single die 6 showing highly repetitive circuit patterns within the die 6 for consecutively increasing magnifications. Although they are of rectangular shape as shown in FIGS. 2A-2C, die circuit patterns 8 are assumed for purposes of simplifying the following discussion to be of square shape with about between 1 to 50 micron sides.

With reference to FIG. 1A, the inspection system 2 includes a laser source 10 that provides a beam of monochromatic light 12 that strikes a mirror 14 which deflects the beam 12 to a Fourier transform lens 16. The Fourier transform lens 16 is located approximately one focal length away from the surface of the semiconductor wafer 4. In FIG. 1A, the Fourier transform lens is shown as one lens, but, as will be shown and discussed in conjunction with FIG. 3A, the lens 16 consists of multiple elements. As the beam 12 passes through the Fourier transform lens 16, the Fourier transform lens 16 collimates the beam of monochromatic light 12. The semiconductor wafer 4 is positioned on the object or frontal focal plane 18 of the Fourier transform lens 16, and the nearly collimated beam of monochromatic light 20 illuminates the patterned surface of the semiconductor wafer 4. Specifically, the nearly collimated beam of monochromatic light 20 illuminates, referring now to FIG. 1B, an elliptical inspection area 22 on the surface of the semiconductor wafer 4 which contains a plurality of die circuit patterns therein. A line normal with respect to the semiconductor wafer 4 that intersects the semiconductor wafer 4 at the center 24 of the elliptical inspection area 22 and runs on the optic axis of the Fourier transform lens 16 defines an optic axis 26.

Referring once again to FIG. 1A, the nearly collimated monochromatic beam of light 20 strikes the semiconductor wafer 4 at an angle ($\Theta$) with respect to the optic axis 26. This angle ($\Theta$) is selected to illuminate semiconductor wafer 4 sufficiently so that the die circuit patterns can be inspected and so that a broad, non-repetitive, spatial frequency spectrum can enter into the inspection system 2. For this inspection system 2, these requirements mean that the angle ($\Theta$) should be as large as possible.

The light 28a reflected and the light 28b and 28c diffracted from the inspection area 22 of the semiconductor wafer 4 which is at angles with respect to the optic axis 26 of between zero degrees and a predetermined maximum angle passes through the Fourier transform lens 16. (The light 28a represents light produced by zero order diffraction, i.e., reflection; and the light 28b and 28c represent light diffracted by the die circuit pattern and a defect, respectively.) The diffracted light that passes through the Fourier transform lens 16 forms the Fourier transform pattern 30 of the illuminated semiconductor wafer surface in the Fourier transform plane 32 located one focal length away from the Fourier transform lens 16. The light rays 30a, 30b, and 30c form the Fourier transform pattern, which comprises an array of bright spots of light that are distributed in the Fourier transform plane 32 in a predictable manner as will be described below in conjunction with FIG. 4.

A previously fabricated filter 34 is positioned symmetrically about the optic axis 26 and in the Fourier transform plane 32. The spatial filter 34 can be fabricated in situ by exposing a recording medium, such as a photographic plate, to light diffracted by the die circuit patterns 8. This can be accomplished with an nonerror-free wafer because the defect information carried by light of relatively low intensity from defects would not expose the photographic plate while Fourier transformed information carried by the relatively high intensity light from die circuit patterns exposes the photographic plate. The spatial filter 34 can also be fabricated in accordance with known computer generation techniques.

The spatial filter 34 blocks the spatial frequencies of light 30a representing the zero order diffracted light and of light 30b representing the error-free Fourier transform of the illuminated die circuit patterns 8 in the inspection area 22, but allows the passage of light 30c originating from possible defects in the die circuit patterns 8. The defect carrying light 36c not blocked by the spatial filter 34 strikes an inverse Fourier transform lens 38 that is shown schematically as a single lens but which is in fact several lens elements (not shown). The inverse Fourier transform lens 38 performs the inverse Fourier transform on the filtered light pattern of the illuminated dies in the inspection area 22. The inverse Fourier transform lens 38 is positioned symmetrically about the optical axis 26 and at some distance behind the Fourier transform plane 32.

A photodetector array 40 is centrally positioned about optic axis 26 in an image plane 42 and receives the light 39c carrying the image of the defects present in the die circuit patterns 8. The image plane 42 is located near the back focal plane of the inverse Fourier transform lens 38. The photodetector array 40 receives the image of the defects present in the wafer dies within the inspection area 22, converts them into digital data, and provides the digital data to a computer 46. The computer 46 analyzes the data to discriminate and classify any irregularities in the inspection area 22 on the surface of the semiconductor wafer 4.

Referring now to FIG. 3 where like numerals designate previously described elements in FIG. 1, the embodiment of the inspection system 2' of the present invention is shown in greater detail. Specifically, the individual lenses and the relevant technical data about each lens that make up the Fourier transform lens 16' are described along with a translation stage 48 that moves the semiconductor wafer 4' relative to the collimated beam of monochromatic light 20', which is also described.

Figure 3B:
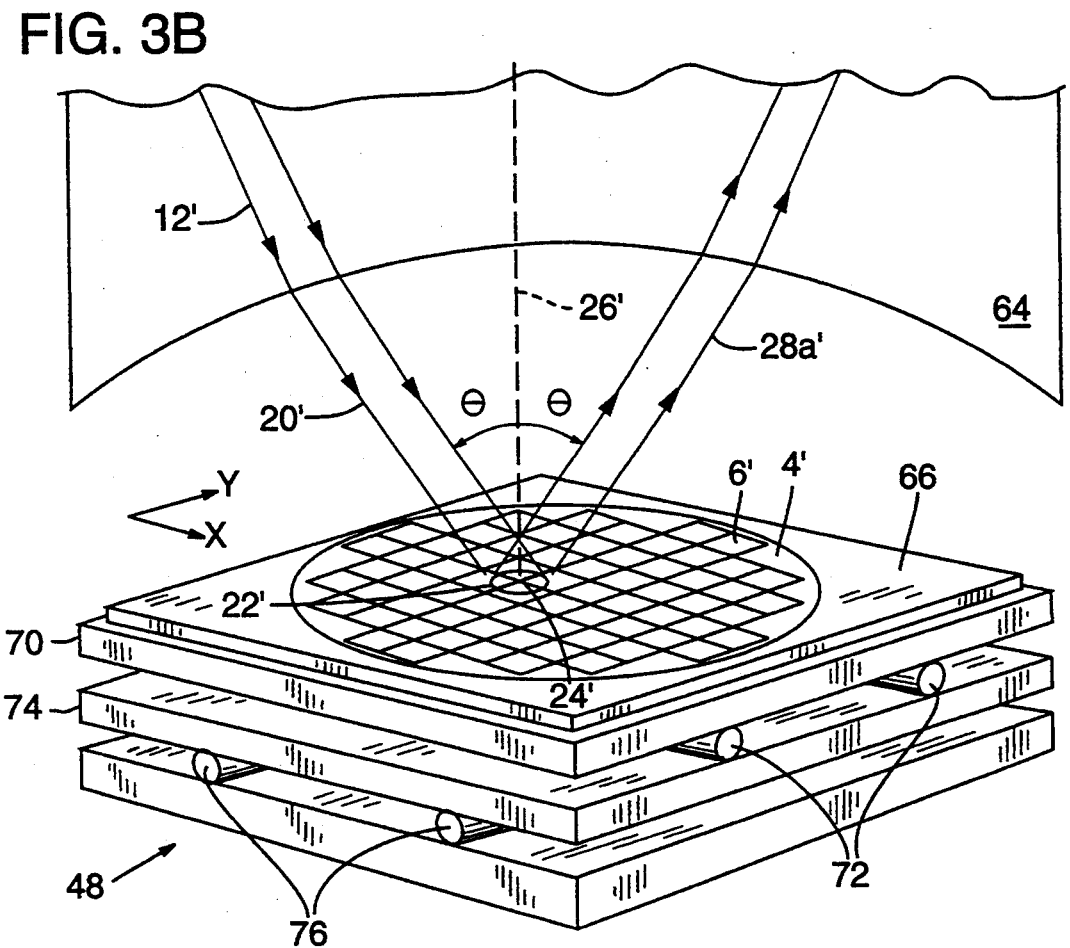
FIG. 3B is a perspective drawing which is useful to the manner in which the semiconductor wafer is illuminated by and moves relative to the inspection system shown in FIG. 3A.

With reference now to FIG. 3A, the inspection system 2' includes a laser 10' that provides a 488 nanometer wavelength monochromatic beam of light 12' that is approximately 3 millimeters in diameter. The beam of monochromatic light 12' deflects off a prism 50, through a lens 52, and towards the Fourier transform lens 16'. The purpose of the prism 50 and the lens 52 is to make the beam of monochromatic light 12' appear, relative to the front focal plane 18', as a point source 54 which is located on the Fourier transform plane 32'. The focal plane of the Fourier transform lens section 16' is positioned a distance of one focal length away from the lens 52 to provide a nearly collimated beam of monochromatic light 20' that strikes the patterned surface of the wafer 4' (FIG. 3B). The semiconductor wafer 4' is mounted in a chuck 66 that constitutes part of a two-dimensional translation stage 48. The wafer 4' is positioned in the object or front focal plane 18' of the Fourier transform lens section 16' and the nearly collimated beam of monochromatic light 20' illuminates the patterned surface of the wafer 4'. The nearly collimated beam of monochromatic light 20' illuminates a 5 millimeter diameter area of the surface of the wafer 4', known as the inspection area 22'.

Referring now to FIG. 3B, the nearly collimated beam of monochromatic light 20' strikes the semiconductor wafer 4' at an angle ($\Theta$) with respect to the optic axis 26'. In the embodiment shown in FIG. 2, this angle ($\Theta$) can be as small as zero degrees and as large as the predetermined maximum angle. For the embodiment shown in FIG. 2, the maximum predetermined maximum angle is the angle formed when the beam of monochromatic light 20' is as far away from the optic axis 26' as possible yet still within the numerical aperture of the lens section 16'. Typically, for the embodiment shown in FIG. 3, an angle ($\Theta$) of about 22.5 degrees for a 3 millimeter diameter beam allows the system to collect a broad spatial frequency spectrum.

More specifically, referring once again to FIG. 3A, the Fourier transform lens section 16' is designed to meet the following three design requirements. First, the Fourier transform lens section 16' together with inverse Fourier transform lens 38' forms an image of sufficient resolution in image plane 42' so that defects accentuated by the Fourier filtering process are focused small enough for adequate signal-to-noise ratio detection. Second, the spot sizes in the Fourier transform plane 32' of the Fourier transform lens section 16' are small enough, relative to their separation, so that the spatial filter 34' transmits diffracted light having an adequate signal-to-noise ratio so that the detector 40' can detect defects. Third, the focal length of the Fourier transform lens section 16' produces a Fourier transform of sufficient scale so that registration of the spatial filter 34' with the Fourier transform plane 32' is practical.

In particular, the lens design of the Fourier transform lens section 16' consists of two groupings. Each grouping of lenses is positioned along and centered about the optic axis 26'. A first group of lenses consisting of a plano convex lens 62 and a double concave lens 64 corrects for excessive coma but introduces only minor power into the lens section 16'. A second group of lenses consisting of a double concave lens 54, a plano convex lens 56, a double convex lens 58, and a negative meniscus lens 60 focuses the reflected light 30a' and diffracted light 30b' and 30c' on the Fourier transform plane 32'. The second group of lenses also collimates the diffracted light 36c' for collection by the inverse Fourier transform lens 38' and corrects for aberrations so as to ensure an adequate signal-to-noise ratio for the spots on the Fourier transform plane 32'.

Tables I and II summarize the design specifications for and the spacing between adjacent elements of the Fourier transform lens section 16'. The surfaces A-M correspond in general to the lettered surfaces in FIG. 3A, in which surface "A" corresponds to the object focal plane 18' and the surface "M" corresponds to the double concave lens 64. In each instance, the radius and the aperture diameter of the surface are given and the shape of each surface is spherical, except for surfaces "D" and "K" which are flat. A positive radius for a surface indicates the center of curvature is to the top in the drawing and a negative radius indicates the center of curvature is to the bottom in the drawing. Dimensions are given in millimeters and the axial distance to the next surface is measured from bottom to top in FIG. 3A.

TABLE 1

| Surface | Radius of Curvature | Axial Distance to Next Surface | Aperture Diameter |
|---|---|---|---|
| A | Infinity | 5.670311 | 10 |
| B | −59.36 | 12.95353 | 47.6 |
| C | 78.257 | 2 | 47.6 |
| D | Infinity | 15.18587 | 47.6 |
| E | −45.72 | 52.7006 | 47.6 |
| F | −123.19 | 19.91053 | 101.6 |
| G | −62.027 | 0.3307335 | 101.6 |
| H | 192.913 | 16.64789 | 101.6 |
| I | −192.913 | 1.163321 | 101.6 |
| J | 125.095 | 17.79352 | 101.6 |
| K | Infinity | 5.988601 | 101.6 |
| L | −183.794 | 7.277428 | 101.6 |
| M | 76.251 | 8.66013 | 101.6 |

TABLE 2

| | |
|---|---|
| Surface D | |
| Index of Refraction | 1.80533 |
| Abbe Number | 25.39 |
| Surface F | |
| Index of Refraction | 1.63603 |
| Abbe Number | 35.34 |
| Surface H | |
| Index of Refraction | 1.69944 |
| Abbe Number | 30.07 |
| Surface J | |
| Index of Refraction | 1.69944 |
| Abbe Number | 30.07 |
| Surface L | |
| Index of Refraction | 1.62512 |
| Abbe Number | 35.7 |

Figure 4:
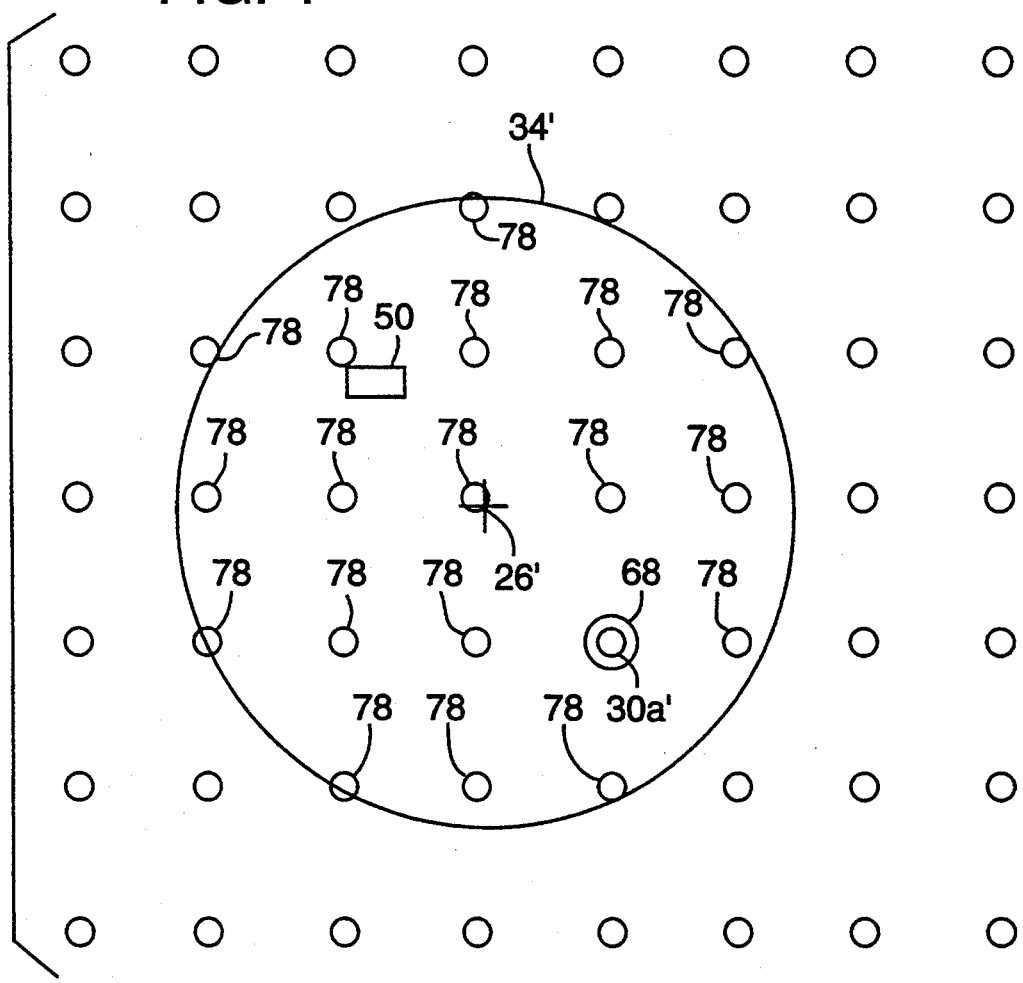
FIG. 4 is a cross sectional drawing of the block diagram of FIG. 3A as seen from 4—4.

The light 28b' and 28c' diffracted from the inspection area 22' passes through the Fourier transform lens section 16'. The Fourier transform lens section 16' transforms the angular differences in the diffracted light 28b' and 28c' at the object plane 18' into spatial differences in the Fourier transform plane 32'. FIG. 4 illustrates the spatial differences in the diffracted light in the Fourier transform plane 32'. Specifically, the zeroth order diffracted light 30a' enters and remains in a light trap 68; first, second, and third order diffracted light 78 from the die circuit pattern strikes the spatial filter 34' to collectively define a regular array of spots; and light 82 diffracted by a nonperiodic defect strikes the spatial filter 34' at a location not coincident with one of the spots in the array.

Referring once again to FIG. 3A, the spatial filter 34', positioned in the plane of the Fourier transform plane 32', blocks the spatial frequencies of the error-free Fourier transform of the illuminated die pattern circuits 8, but allows the passage of light originating from possible defects in the die circuit patterns. The defect carrying light 36c' not blocked by the spatial filter 34' strikes the inverse Fourier transform lens 38' which performs the inverse Fourier transform on the defect carrying light 36c'. The photodetector array 40' receives the light 39c' carrying the image of the defects present in the die circuit patterns within the inspection area 22', converts them into digital data, and provides the digital data to the computer 46' which analyzes the data to discriminate and quantify any irregularities.

The magnification of the inverse Fourier transform lens 38' is of an amount that approximately matches the resolution limit of the image to the pixel size of the photodetector array 40'. In particular, the photodetector array 40' has a light sensitive surface 44 whose dimensions are about 13 millimeters × 3.25 millimeters and an approximately 13 micrometer pixel size. A 10-fold magnification is, therefore, the proper amount to match the object plane 18' resolution of 1.0 micron from the Fourier transform lens 16' to the 13 micrometer pixel size of the photodetector array 40'.

To inspect the entire patterned surface of the wafer 4', translation stage 48 sequentially moves each portion of the wafer 12 under the inspection area 22' for illumination by the laser 10'. The area of the light sensitive surface 44' of the stationary photodetector array 40' limits the amount of light detected to that of a portion of the image corresponding to only the wafer 4' centered about the inspection area 20'. The movement of translation stage 40' is continuous in a stripe-to-stripe serpentine fashion to implement a time delay integration technique for collecting the defect information for each die on the patterned surface of the wafer 4'. The determination of the presence of defects in the wafer 4' is accomplished by partitioning the wafer 4' into striped regions (not shown) of 1.3 millimeters in width and moving translation stage 40 in a serpentine scan fashion so that the 3 millimeter diameter spot emanating from the laser 10' illuminates stripe-by-stripe the entire surface of wafer 4'. The 3 millimeter spot diameter magnifies to 6 millimeters by the time the light emanating from laser 10' reaches the wafer 4'.

Translation stage 48 comprises an X-Y positioning table that is capable of positioning the wafer 4' on the inspection area 22' for illumination by the 6 millimeter diameter beam of collimated, monochromatic light 20'. Referring to FIG. 3B, a top or Y-stage 70 of translation stage 48 supports chuck 66 and moves wafer 4' along the Y direction on rollers 72. A bottom or X stage 74 moves wafer 4' along the X direction on rollers 76. One suitable type of X-Y positioning table is a Model 8500 manufactured by Kensington Laboratories, Inc. of Richmond, Calif.

A control circuit (not shown) for translation stage 48 keeps wafer 4' moving at a constant speed as it positions each stripe region (not shown) for illumination by the laser 10'. Translation stage 48 provides position coordinate information indicating the position of translation stage 48 and the position of defects in the corresponding defect image relative to a known location on the wafer 4'. The detection of image defects is performed in accordance with a time delay integration technique which is described fully in U.S. Pat. No. Re. 33,956. It is also obvious to one skilled in the art that an air table (not shown) could replace the translation stage 48 and sequentially move each portion of the wafer 12' under the inspection area 22'.

Figure 5:
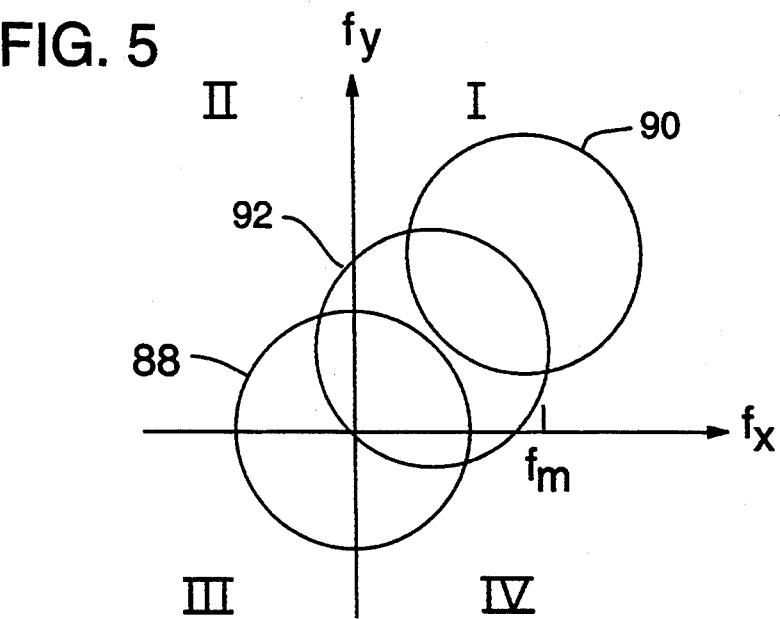
FIG. 5 is an exemplary Fourier transform plane which is useful in describing the operation of the embodiment of the invention.

The system shown in FIGS. 1 and 3 collects a broad spatial frequency spectrum which allows the system to detect a broad range of different sized defects. FIG. 5 shows the collected spatial frequency spectrums in the Fourier transform plane for various different inspection systems. The system disclosed in U.S. Pat. No. Re. 33,956 collects the spatial frequencies within the circle 88. Because the defects on the wafer can be considered planar, the defect spatial frequency spectrum is considered symmetrical along both the $f_x$ and $f_y$ axis in FIG. 5 so that the spatial frequency spectra in the four quadrants I, II, III, and IV in FIG. 5 are identical. Accordingly, the system disclosed in U.S. Pat. No. Re. 33,956 fails to use the maximum collection capability of the lens system because the presence of redundant low spatial frequency information within the four quadrants inhibits detection of defect information carried by the highest spatial frequencies. The system disclosed in U.S. Pat. No. 5,177,559 does not similarly carry redundant information but collects within the circle 90 only the spatial frequency components that are in the higher range. This system may, however, fail to detect some of the relatively large defects having more relatively low-frequency components.

The disclosed system obviates the problems associated with the above-identified systems by avoiding redundancy and collecting low, mid-level, and relatively high spatial frequencies within the circle 92. Accordingly, this system can detect a broad range of defect sizes from very small sized defects that have relatively high spatial frequencies associated with them to large sized defects that have relatively low spatial frequencies associated with them.

Moreover, this system can be optimized for detecting a specific range of defect sizes. By moving the angle ($\Theta$) with respect to the optic axis 26 at which the collimated beam of monochromatic light 20 strikes the wafer 4, the system will collect a different spatial frequency spectrum for each angle. Specifically, the larger the angle ($\Theta$), the more spatial frequency components in the higher frequency range will be collected at the expense of collecting fewer spatial frequency components in the lower frequency range. Thus, if a specific range of defect sizes is anticipated for a group of wafers to be inspected, then the system can be optimized by setting the angle ($\Theta$) at which the collimated beam of monochromatic light strikes the wafer to the angle ($\Theta$) that allows the system to collect those spatial frequencies that are best representative of the anticipated range of defects sizes.

Other embodiments of the invention including additions, subtractions, deletions, and other modifications of the preferred disclosed embodiments of the invention will be obvious to those skilled in the art and are within the scope of the following claims.

We claim:

1. A method of locating defects in a repetitive pattern on a surface, comprising the steps of:
   illuminating through a lens the surface with a nearly collimated beam of monochromatic light at an angle with respect to the normal of the surface, the light being diffracted from the surface and the angle being set to result in the diffracted light having a specific spatial frequency spectrum that is associated with specific sized defects in the repetitive pattern,
   capturing light diffracted from the surface at angles with respect to the normal of the surface that allow the lens to collect spatial frequencies contained in the spatial frequency spectrum associated with the specific sized defects;
   spatially filtering the captured light to attenuate spatial frequencies corresponding to the repetitive pattern relative to spatial frequencies corresponding to nonrepetitive patterns; and
   focusing the spatially filtered light into an image, wherein images of nonrepetitive patterns are accentuated relative to images of the repetitive pattern.

2. The method of claim 1 further comprising the step of moving the surface relative to the nearly collimated beam of monochromatic light.

3. The method of claim 1 wherein the step of capturing further includes the step of generating Fourier transform light from the captured light.

4. The method of claim 1 wherein the step of spatially filtering further includes the step of generating an inverse Fourier transform of spatially filtered light from the spatial frequencies not blocked by the spatial filtering.

5. A method of detecting defects in a specimen, the specimen including a die, wherein the die has many redundant circuit patterns, comprising the steps of:
   illuminating through a lens an inspection area on the specimen with a nearly collimated beam of monochromatic light, the inspection area having a plurality of die circuit patterns located thereon, and the incident beam of monochromatic light striking the specimen at an angle with respect to the normal of the specimen and being diffracted from the specimen, the angle set to a value that results in the diffracted light having a specific spatial frequency spectrum that is associated with specific sized defects in the die circuit patterns;
   transforming light diffracted from the inspection area at angles with respect to the normal of the specimen into Fourier transformed light having spatial frequencies contained in the spatial frequency spectrum associated with the specific sized defects;
   spatially filtering the Fourier transformed light so as to attenuate the spatial frequencies which conform to the spatial frequenies of an error-free reference pattern corresponding to the die circuit pattern; and
   collecting the spatilly filtered light so as to form an image of defects corresponding to the plurality of die circuit patterns within the inspection area.

6. The method of claim 5 which further comprises the step of changing the position of the specimen relative to the position of the nearly collimated beam of monochromatic light so that different ones of the die circuit patterns are positioned in the inspection area, thereby collecting the spatial frequencies of all of the different ones of the die circuit patterns in the die.

7. The method of claim 6 further comprising the step of processing all of the spatial frequencies of all of the different ones of the die circuit patterns in the die so as to determine the size and location of the defects on the die.

8. The method of claim 5 further including an illuminating means, the illuminating means and the lens emitting the nearly collimated beam of monochromatic light, the method further comprising the steps of:
   defining, the respect to the specimen, a plurality of adjacent strips, each strip including a series of adjacent die circuit patterns;
   moving the specimen and the nearly collimated beam of monochromatic light relative to each other along the length of each strip so as to illuminate all the die circuit patterns within each strip; and
   processing the unblocked spatial frequencies corresponding to the die circuit patterns within each strip so as to determine the location and size of defects in an individual strip.

9. The method of claim 5 wherein the step of collecting further includes the step of generating an inverse Fourier transform from the spatially filtered light.

10. An apparatus for detecting defects in a specimen, the specimen including a die, wherein the die has many redundant die circuit patterns, comprising:
    a laser for generating a nearly collimated beam of monochromatic light onto an inspection area on the specimen which encompasses a plurality of die circuit patterns, the light striking the inspection area at an angle with respect to the normal of the inspection area and being diffracted from the inspection area, and the angle being set to result in the diffracted light having a specific spatial frequency spectrum that is associated with specific sized defects in the die circuit patterns located in the inspection area;
    a lens for capturing light diffracted from the inspection area for generating Fourier transformed light from the capture diffracted light, the nearly collimated beam of monochromatic light travelling through the lens before striking the inspection area at an angle with respect to the normal of the specimen that results in diffracted light having spatial frequencies contained in the specific spatial frequency spectrum associated with the specific sized defects;
    a spatial filter for collecting the Fourier transformed light and attenuating the spatial frequencies which conform to the spatial frequencies of an error-free reference pattern corresponding to the die circuit patterns; and
    a light-sensitive detector for collecting the spatially filtered light not blocked by the spatial filter so as to form an image of defects in the inspection area.

11. The apparatus of claim 10 further comprising means for changing the position of the specimen relative to the nearly collimated beam of monochromatic light so that all of the different ones of the die circuit patterns are positioned in the inspection area thereby capturing the spatial frequencies of all of the different ones of the die circuit patterns in the die.

12. The apparatus of claim 10 further comprises processing means for processing all of the spatial frequencies of all of the different ones of the die circuit patterns in the die so as to determine the location and size of defects.

13. The apparatus of claim 10 further includes defining, with respect to the specimen, a plurality of adjacent strips, each strip including a series of adjacent die circuit patterns, the apparatus further comprising:
    means for moving the specimen and the nearly collimated beam of monochromatic light relative to each other along the length of each strip so as to collect the unblocked spatial frequencies corresponding to the die circuit patterns within each strip; and
    processing means for processing the collected unblocked spatial frequencies corresponding to the die circuit patterns within each strip so as to determine the location and size of defects in an individual strip.

14. The apparatus of claim 10 wherein the spatial filter further comprises an inverse Fourier transform means for collecting the spatially filtered light not blocked by the spatial filter and for generating inverse Fourier transform and spatially filtered light.

15. The apparatus of claim 10 wherein the optical filter further comprises relatively transparent and nontransparent portions, the relatively nontransparent portions conforming to the spatial frequencies of an error-free reference corresponding to the die circuit pattern.

16. A method of positioning a beam of monochromatic light ti illuminate a surface having a repetitive pattern thereon so specific spatial frequency spectrum associated with specific sized defects in the repetitive pattern on the surface, comprising the steps of:
    illuminating the surface with a beam of monochromatic light;
    moving the beam of monochromatic light to various different angles with respect to the normal of the surface;
    collecting the light that is diffracted from the surface at each of the various different angles, the diffracted light containing the spatial frequency spectrum of the defects in the pattern on the surface which are illuminated by the beam of monochromatic light striking the surface at a specific angle with respect to the normal of the surface; and
    positioning the beam of monochromatic light with respect to the normal of the surface to the angle that produces diffracted light which contains the specific spatial frequency spectrum associated with the specific sized defects in the pattern on the surface.

17. The method of claim 16 wherein the step of collecting the light that is diffracted further comprises the steps of:
    generating Fourier transformed light from the captured light; and
    spatially filtering the Fourier transformed light to attenuate spatial frequencies corresponding to the repetitive pattern relative to the spatial frequencies corresponding to nonrepetitive patterns.

18. The method of claim 16 further comprising the steps of;
    illuminating the surface with a nearly collimated beam of monochromatic light at the angle with respect to the normal of the surface;
    capturing light diffracted from the surface;
    spatially filtering the captured light to attenuate spatial frequencies corresponding to the repetitive pattern relative to spatial frequencies corresponding to nonrepetitive patterns; and
    focusing the spatially filtered light into an image, wherein images of nonrepetitive patterns are accentuated relative to images of the repetitive pattern. beam of monochromatic light.

19. The method of claim 18 wherein the step of capturing further includes the step of generating Fourier transformed light from the captured light.

20. The method of claim 18 wherein the step of spatially filtering further includes the step of generating inverse Fourier transform, spatially filtered light from the spatial frequencies not blocked by the spatial filtering.

21. The method of claim 16 further comprising the step of moving the surface relative to the nearly collimated beam of monochromatic light.

* * * * *

UNITED STATES PATENT AND TRADEMARK OFFICE
CERTIFICATE OF CORRECTION

PATENT NO. : 5,428,442  
DATED : June 27, 1995  
INVENTOR(S) : Lawrence H. Lin and Victor A. Scheff Page 1 of 2

It is certified that error appears in the above-indentified patent and that said Letters Patent is hereby corrected as shown below:

Abstract, line 5, delete ")" after "28b".

Column 3, line 57, delete ";" after "defects".

Column 5, line 49, delete "," after "the".

Column 11, line 58 of Claim 8, change "the" (first occurrence) to --with--.

Column 12, line 19 of Claim 10, insert --and-- before "for".

Column 12, line 20 of Claim 10, change "capture" to --captured--.

Column 13, line 7 of Claim 16, change "ti" to --to--.

Column 13, line 8 of Claim 16, insert after "so" --that light which is diffracted from the surface has a--.

UNITED STATES PATENT AND TRADEMARK OFFICE
CERTIFICATE OF CORRECTION

PATENT NO. : 5,428,442
DATED : June 27, 1995
INVENTOR(S) : Lawrence H. Lin and Victor A. Scheff It is certified that error appears in the above-indentified patent and that said Letters Patent is hereby corrected as shown below:

Column 13, line 27 of Claim 16, before "specific" insert --spacial frequency spectrum which is closest to the--.

Column 14, line 8 of Claim 18, change ";" to --:--.

Column 14, line 20 of Claim 18, delete "beam of monochromatic light.".

Signed and Sealed this

Thirteenth Day of February, 1996

Attest:

BRUCE LEHMAN

Attesting Officer    Commissioner of Patents and Trademarks